US00PP19939P2

(12) United States Plant Patent
Cho

(10) Patent No.: US PP19,939 P2
(45) Date of Patent: Apr. 21, 2009

(54) ***COLOCASIA* PLANT NAMED 'DIAMOND HEAD'**

(50) Latin Name: *Colocasia esculenta*
Varietal Denomination: DIAMOND HEAD

(76) Inventor: John Cho, P.O. Box 269, 424 Mauna Pl., Kula, HI (US) 96790

( * ) Notice: Subject to any disclaimer, the term of this patent is extended or adjusted under 35 U.S.C. 154(b) by 0 days.

(21) Appl. No.: 12/006,579

(22) Filed: Jan. 4, 2008

(51) Int. Cl.
*A01H 5/00* (2006.01)

(52) U.S. Cl. ..... Plt./373

(58) Field of Classification Search ..... Plt./373
See application file for complete search history.

*Primary Examiner*—S. B McCormick Ewoldt

(57) ABSTRACT

A new cultivar of *Colocasia* plant named 'DIAMOND HEAD' that is characterized by a combination of large dark purple to black leaves with a glossy finish and a small circular-shaped dark burgundy colored 'piko' and semi-glossy dark burgundy colored petioles. In combination these characteristics distinguish 'DIAMOND HEAD' from all other varieties of *Colocasia* known to the inventor.

5 Drawing Sheets

Genus: *Colocasia.*
Species: *esculenta.*
Denomination: 'DIAMOND HEAD'.

BACKGROUND OF THE INVENTION

The present invention relates to a new and distinct variety of *Colocasia* commonly known as the taro plant or elephant ears. *Colocasia* is grown as a food crop or for use as an ornamental for container or the landscape. The new cultivar is known botanically as *Colocasia esculenta* and will be referred to hereinafter by the cultivar name 'DIAMOND HEAD'. 'DIAMOND HEAD' is one of is one of five co-pending applications by the inventor relating to new cultivars of *Colocasia.* The other four co-pending applications are titled *Colocasia* plant named 'Hawaiian Eye' (U.S. application Ser. No. 12/006,580), *Colocasia* plant named 'Blue Hawaii' (U.S. application Ser. No. 12/006,576), *Colocasia* plant named 'Pineapple Princess' (U.S. application Ser. No. 12/006,581), and *Colocasia* plant named 'Hilo Bay' (U.S. application Ser. No. 12/006,474).

*Colocasia* is a tuberous rooted perennial which is native to tropical Asia and Polynesia. It grows to 1.5–2 m in height from starchy tubers. The leaves of *Colocasia* are heart-shaped and very large in size. The tuberous roots are cooked and eaten as a starchy staple in many tropical areas. It is also grown as ornamental plants for the landscape in warmer climates or as a container plant in colder areas.

The new *Colocasia* variety named 'DIAMOND HEAD' is the product of a formal breeding program, carried out in a cultivated area in Kula, Hi. The purpose of the breeding program is to develop new commercial varieties by combining attributes not found in currently commercially available varieties.

'DIAMOND HEAD' is a seedling selection from the controlled pollination between the female parent variety 'Putih' (not patented) and male parent variety 'Black Magic' (not patented). Initially designated as '2005-17', 'DIAMOND HEAD' was derived from a single plant selected in 2005.

The new variety 'DIAMOND HEAD' has large dark purple almost black colored leaves with a glossy finish. 'DIAMOND HEAD' produces uniform dark burgundy colored petioles with a semi-glossy finish. The leaves are ⅓ to ½ larger than its female parent and similar in size compared to its female parent, 'Putih'. The female parent, 'Putih' exhibits smaller green glossy leaves with a purple spot on the upper leaf surface at the point of leaf and petiole attachment and a smooth margin. The petioles are of a light green semi-glossy color. The male parent, 'Black Magic', exhibits dark purple to black colored leaves with a matte finish and a smooth margin. The petioles are dark burgundy in color with a matte finish. In these aspects, this new variety differs from its parents.

The closest comparison variety known to the inventor is its female parent 'Black Magic' (not patented), its closest commercial variety. 'DIAMOND HEAD' produces uniform dark purple colored leaves with a glossy finish compared with 'Black Magic' that exhibit dark purple matte finish leaves.

The most commonly employed means of asexual propagation of the genus *Colocasia* is the excision and replanting of a shoot which consists of the apical 1 cm–2 cm portion of the plant corm with the attached basal 15 cm–20 cm portion of the petiole. In regions of the world where *Colocasia* is grown, this plant shoot is known as a "huli", and the means of propagation is known as "huli propagation." Asexual propagation of hulis of 'DIAMOND HEAD' began in 2005 in Hawaii by the inventor using huli propagation whereby the apical shoots are separated from the plant by cutting the shoot at the top of the corm immediately above the newest leaf scar and planted. Evaluation in field and pot studies have shown the unique features of 'DIAMOND HEAD' to be stable, uniform, and reproduces true to type in successive generations of asexual propagation.

SUMMARY OF THE INVENTION

The following traits have been repeatedly observed and represent the distinguishing characteristics of the new *Colo-*

*casia* variety named 'DIAMOND HEAD'. In combination these traits set 'DIAMOND HEAD' apart from all other varieties of *Colocasia* known to the inventor. 'DIAMOND HEAD' has not been tested under all possible conditions and phenotypic differences may be observed with variations in environmental, climatic and cultural conditions, however, without any variance in genotype:

1. 'DIAMOND HEAD' exhibits large saggitate-shaped leaves and slightly undulating margins.
2. The leaves of 'DIAMOND HEAD' are a glossy and dark purple in color.
3. The surface of the leaves of 'DIAMOND HEAD' is a glossy finish.
4. 'DIAMOND HEAD' has semi-glossy dark burgundy colored petioles.

BRIEF DESCRIPTION OF THE DRAWINGS

The accompanying color drawings

Figure 1:
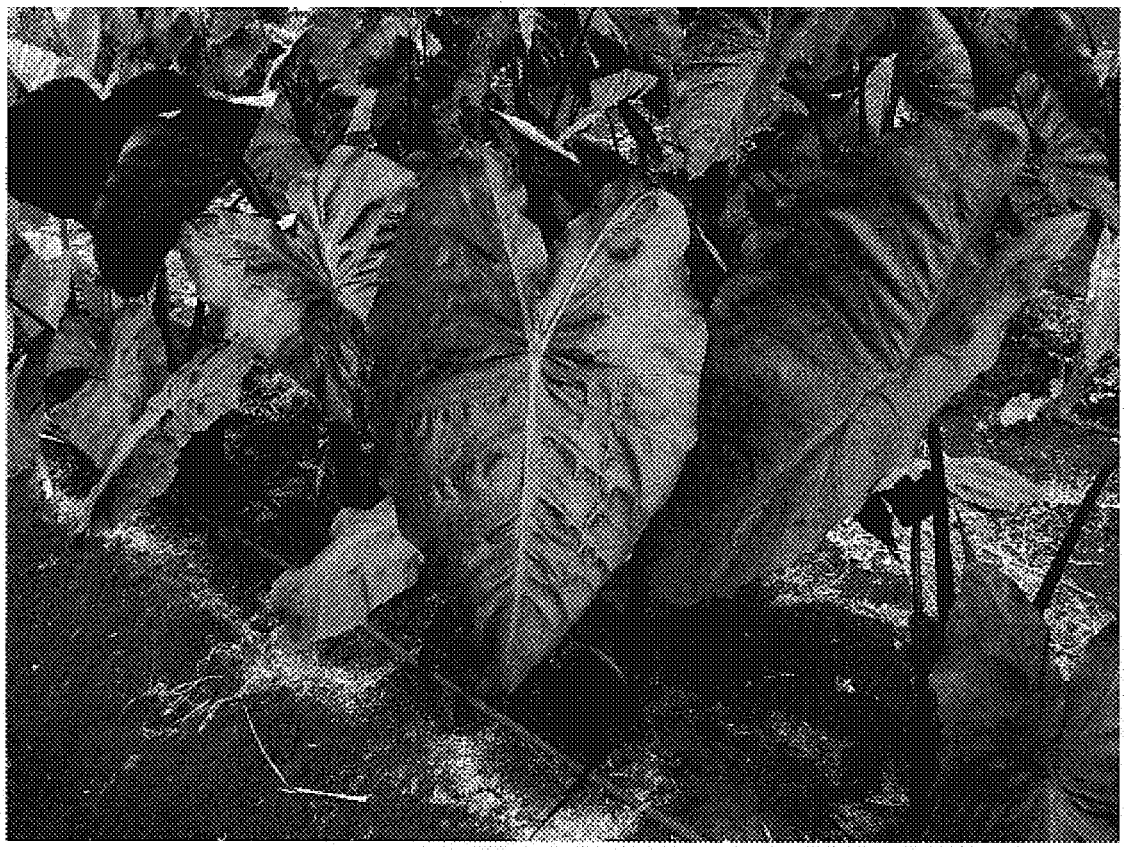
FIGS. 1 to 5 illustrate the overall appearance of 'DIAMOND HEAD' showing the colors as true as it is reasonably possible to obtain in colored reproductions of this type. Colors in the drawing may differ from the color values cited in the detailed botanical description, which accurately describe the actual colors of the new variety 'DIAMOND HEAD'.

The drawing labeled as FIG. 1 shows 'DIAMOND HEAD' grown from a huli after approximately 3 months.

Figure 2:
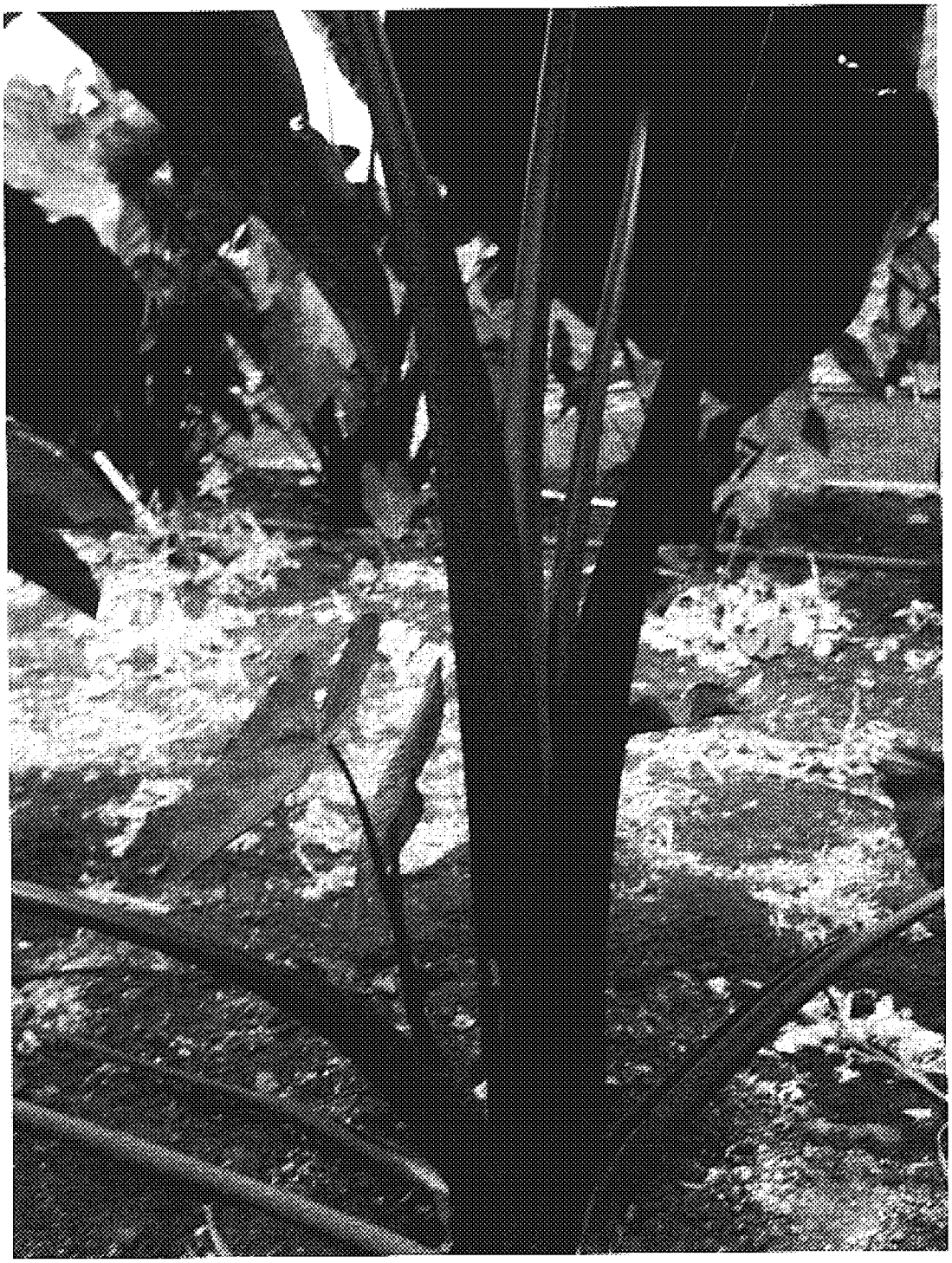

The drawing labeled as FIG. 2 shows the semi glossy dark burgundy colored petioles of 'DIAMOND HEAD'.

Figure 3:
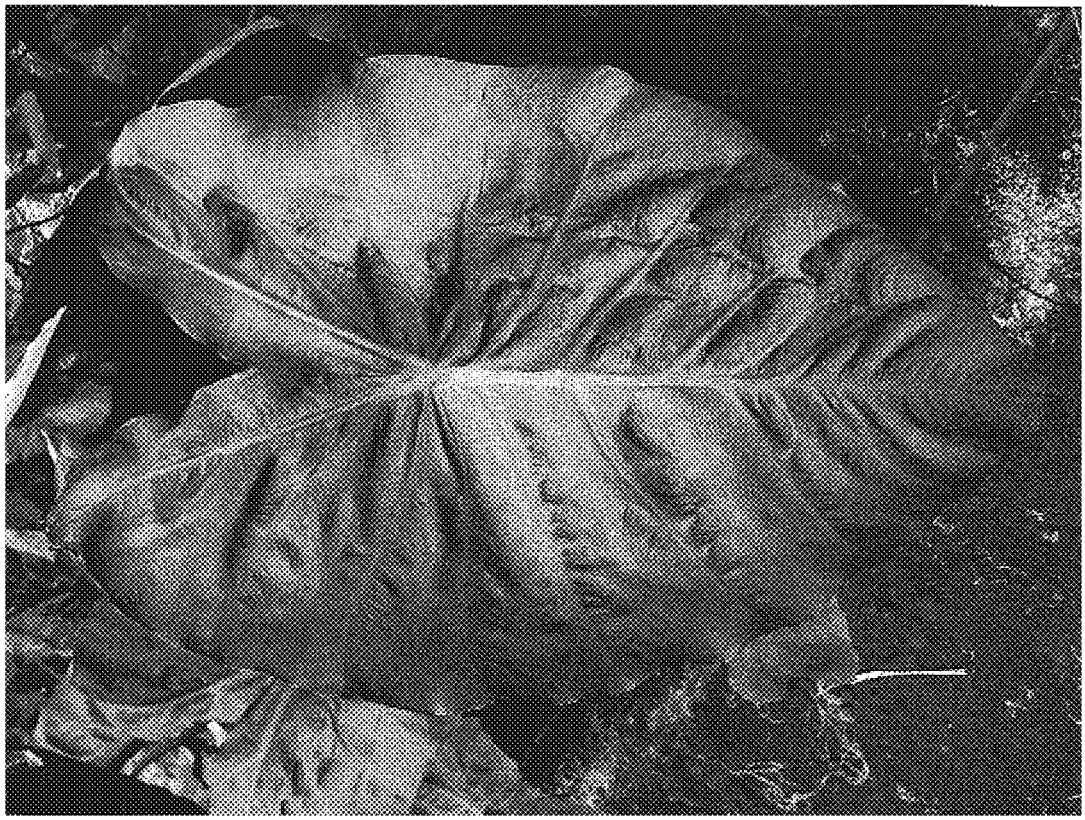

The drawing labeled FIG. 3 illustrates a sagittate 'DIAMOND HEAD' mature leaf blade whose lamina is dark purple to black with a smooth texture and glossy appearance. This drawing also illustrates that part of the leaf which is known as the 'piko' namely the area of upper leaf surface which is present at the junction of the leaf blade with the petiole and from which three principal veins radiate.

Figure 4:
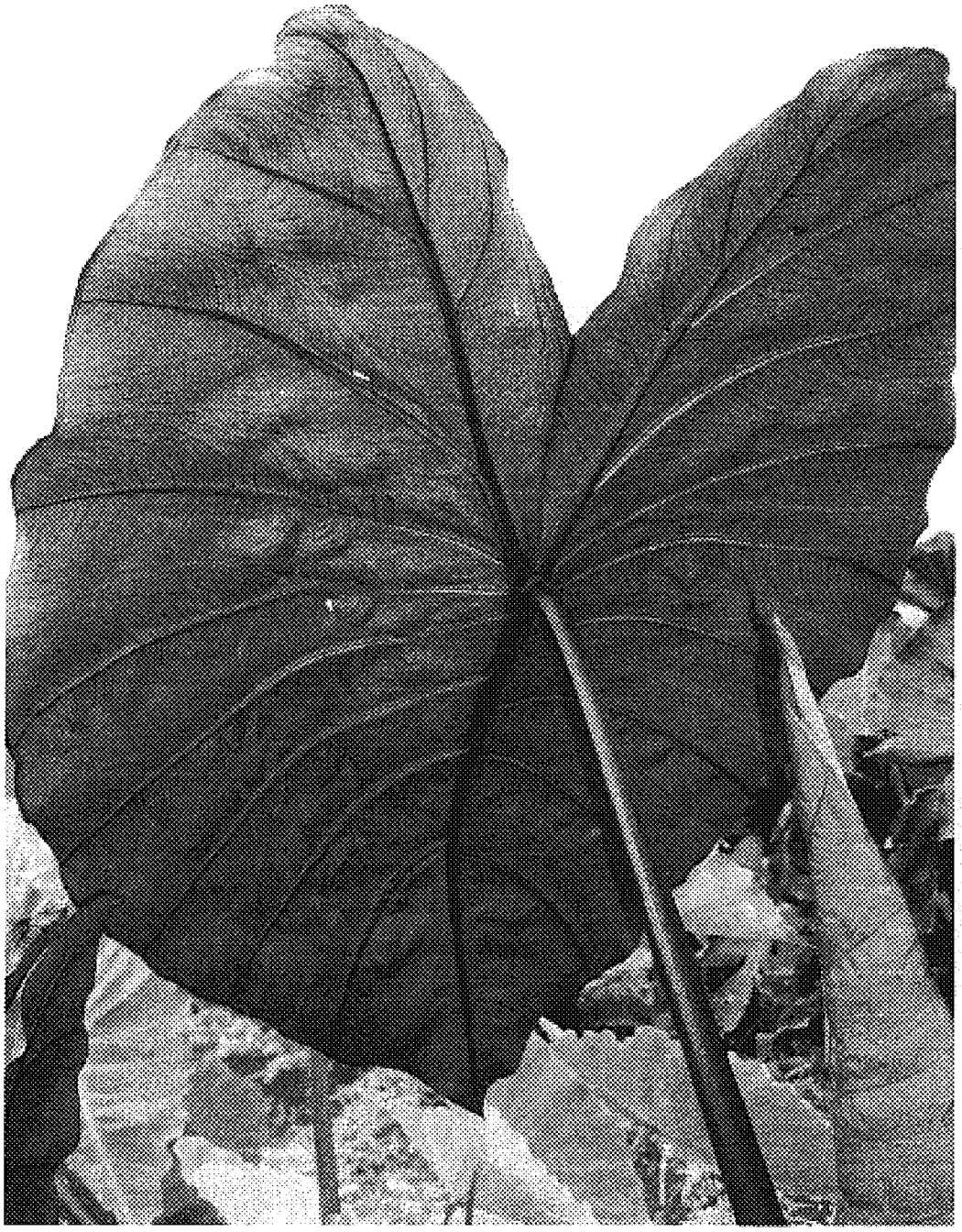

The drawing labeled as FIG. 4 shows the underside of a mature leaf of 'DIAMOND HEAD' with light purple lamina and purple venation.

Figure 5:
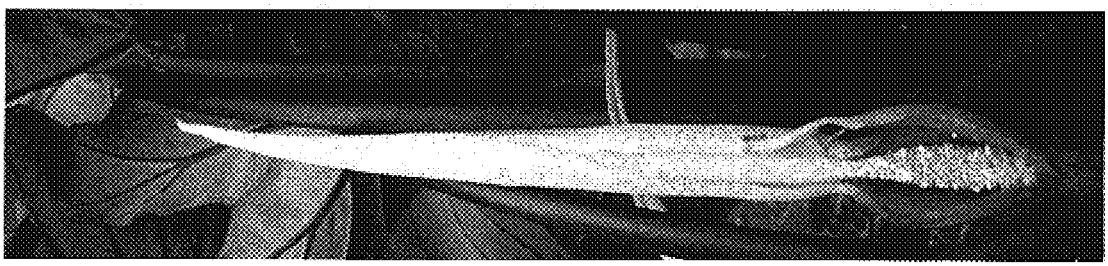

The drawing labeled as FIG. 5 shows the inflorescence or spadix of 'DIAMOND HEAD'.

Figure 6:
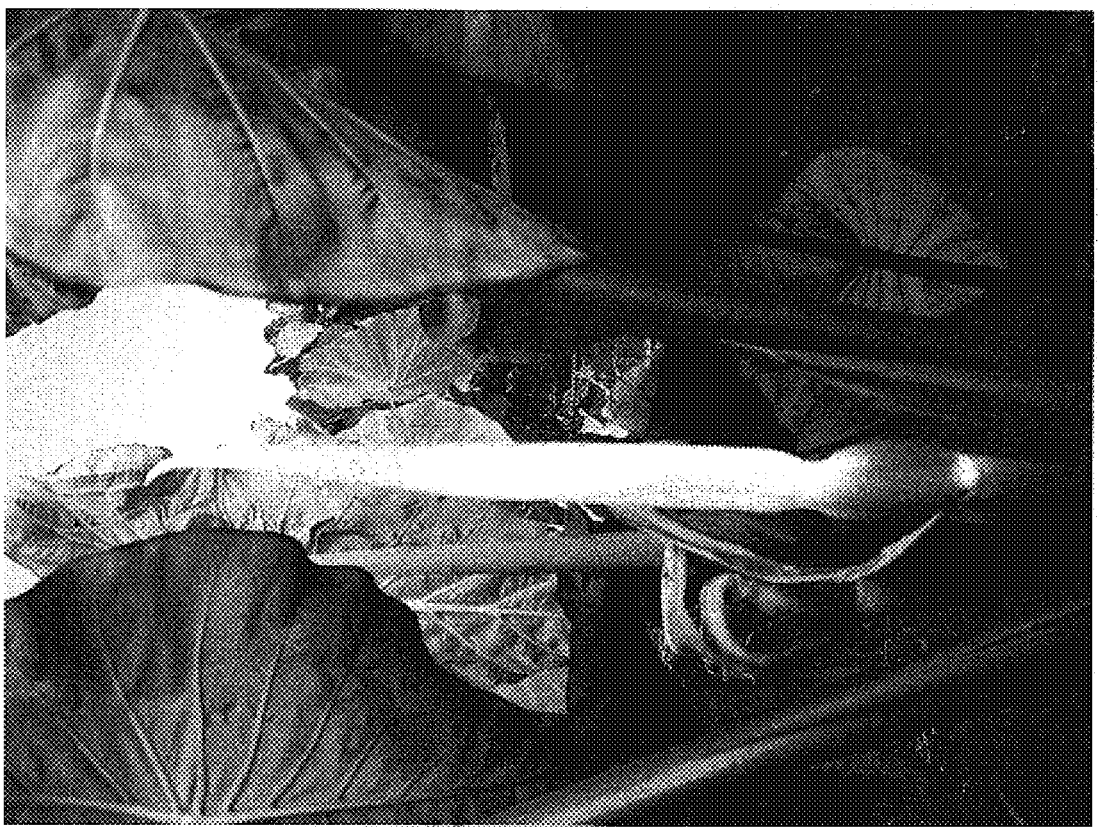

The drawing labeled as FIG. 6 shows the sheath or spathe that normally encloses the spadix.

All drawings have been made from plants which were approximately 3 months old from a division and which have been grown out-of-doors. No growth regulators have been applied.

BOTANICAL DESCRIPTION OF THE PLANT

The following is a detailed description of the new *Colocasia* plant named 'DIAMOND HEAD'. Data was collected from plants that were 3–6 months of age grown outside in Kula, Hi. as indicated. The color determinations are in accordance with the 2001 edition of The Royal Horticultural Society Colour Chart, London, England, except where general color terms of ordinary dictionary significance are used. The growing requirements are similar to other *Colocasia*.

Botanical classification:
Genus: *Colocasia.*
Species: *esculenta.*
Denomination: 'DIAMOND HEAD'.
Common name: Taro or elephant ears.
Plant use: Food, container or landscape plant.
Cultural requirements: Cultural requirements are well draining soil or growing media, full sun to partial shade.
Root system: Fibrous.
Plant vigor: Vigorous.
Parentage:
*Female parent.*—'Putih'.
*Male parent.*—'Black Magic'.
Plant description: The plant has 4–6 suckers closely attached to the mother plant. A "mother plant" is the plant material which is first introduced into the soil to begin production. Typically, this plant material contains part of the huli and 2–3 leaf blades. This produces a "mother corm" which produces lateral shoots called 'cormels' which give rise to daughter plants. Daughter plants begin to appear above soil level about 2–3 months after planting of the mother plant.
Plant dimensions: 990 mm to 1230 mm in height and 785 mm to 1145 mm in width.
Plant hardiness: USDA Zone 7.
Propagation: Propagation is accomplished by huli propagation and by tissue culture.
Propagation: Root formation occurs immediately after transplanting. Propagation is complete when fully rooted. Daughter plants appear above soil level around 2–3 months after huli planting.
Tissue Culture: Time to develop a new plant capable of growing on its own roots: 3 weeks.
Crop time: (from propagation to a saleable 1 gallon container):6–10 weeks at temperatures of 75 degrees Fahrenheit –65 degrees Fahrenheit.
Pest or disease susceptibility and resistance: No more or less susceptible to disease or pests than other cultivars.
Tuberous Roots:
*Dimensions.*—6.7 inches in length, 4.1 inches in diameter. Color 155D.
Foliage:
*Number.*—On average, a 5–6 month old mother plant maintains 5–6 functional leaves at a time, each new leaf is produced approximately every 10 days until the corm matures.
*Petioles.*—Length: Up to 125 cm in length. Width: 10.5 mm (just below attachment to lamina)×21 mm (at the upper sinus)×32 mm (at the middle of the sinus). Color: Mature leaf has a petiole color of 187A and younger leaves have petiole color of 177D. Sap color: Colorless.
*Leaf.*—Dimensions at maturity (5–6 months old): 660 mm in length and 435 mm in width. Aspect: Erect with apex down. Shape: Sagittate lamina. Margins: Entire, slightly undulating. Apex: Pointed. Base: Peltate. Lamina appendages: Absent. Attachment: Petiolate with characteristic tissue formed at junction of leaf blade with the upper termination of the petiole. This area of the leaf tissue is also known as the "piko" and is evident by virtue of its upper surface being the same color as the veins or darker. The principal veins radiate from the piko. Piko color: N187A. Leaf sheaf: Open. Texture: Smooth appears glossy. Leaf color (adaxial surface): Younger leaves are 138B; mature leaves are N147B. Leaf color (abaxial surface): Younger leaves are 198A; mature leaves are N187A. Venation: Palmate. Veins: Three principal veins radiating from the piko. The largest a midrib extending from the piko to the tip of the lamina with up to 13 pairs of secondary veins radiating from it. Vein color (adaxial and abaxial surfaces): 187A.

Flowers and reproductive organs: The inflorescence arises from the leaf axils. The inflorescence is made up of a short peduncle, a spadix, and spathe. The spadix is botanically a spike, with a fleshy central axis to which the small sessile flowers are attached. The spadix is 110 mm to 120 mm long, with female flowers at the base, male flowers towards the tip, and sterile flowers in between, in the region compressed by the neck of the spathe. The extreme tip or appendage of the spadix has no flowers at all. The spathe is a large yellowish bract, 250 mm long, which sheaths the spadix. The lower part of the spathe is green (187D) in color and wraps tightly around the spadix and completely occludes the female flowers from view. The top portion of the spathe is yellow (13C) in color and is rolled inward at the apex, but is open on one side to reveal the male flowers on the spadix. The top and bottom portions of the spadix are separated by a narrow neck region, corresponding to the region of the sterile flowers on the spadix.

What is claimed is:

1. A new and distinct cultivar of *Colocasia* plant named 'DIAMOND HEAD' as described and illustrated herein.

* * * * *

UNITED STATES PATENT AND TRADEMARK OFFICE

CERTIFICATE OF CORRECTION

PATENT NO. : PP19,939 P2
APPLICATION NO. : 12/006579
DATED : April 21, 2009
INVENTOR(S) : John Cho It is certified that error appears in the above-identified patent and that said Letters Patent is hereby corrected as shown below:

On Column 1, line 1, insert the following header and paragraph:

--Statement of Government Interest

This invention was made with Government support under Grant No. 2001-31100-06015/HAW914H awarded by the U.S. Department of Agriculture. The Government has certain rights in this invention.--

Signed and Sealed this
Twenty-ninth Day of November, 2011

David J. Kappos

David J. Kappos
*Director of the United States Patent and Trademark Office*